(12) United States Patent
Guss et al.

(10) Patent No.: US 11,466,296 B2
(45) Date of Patent: Oct. 11, 2022

(54) GENETICALLY-MODIFIED BACTERIA FOR CONVERSION OF ORGANIC COMPOUNDS TO BUTANOL AND METHODS OF USE

(71) Applicant: UT-Battelle, LLC, Oak Ridge, TN (US)

(72) Inventors: Adam M. Guss, Knoxville, TN (US); Lauren A. Riley, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 16/934,359

(22) Filed: Jul. 21, 2020

(65) Prior Publication Data

US 2021/0024965 A1 Jan. 28, 2021

Related U.S. Application Data

(60) Provisional application No. 62/876,886, filed on Jul. 22, 2019.

(51) Int. Cl.
| | |
|---|---|
| *C12P 7/16* | (2006.01) |
| *C12N 9/02* | (2006.01) |
| *C12N 1/20* | (2006.01) |
| *C12R 1/01* | (2006.01) |

(52) U.S. Cl.
CPC ............... *C12P 7/16* (2013.01); *C12N 9/001* (2013.01); *C12N 9/0008* (2013.01); *C12N 1/205* (2021.05); *C12R 2001/01* (2021.05); *C12Y 102/01057* (2013.01); *C12Y 103/01086* (2013.01)

(58) Field of Classification Search
None
See application file for complete search history.

(56) References Cited

U.S. PATENT DOCUMENTS

2019/0330665 A1 10/2019 Elmore et al.

FOREIGN PATENT DOCUMENTS

WO WO-2012135731 A2 * 10/2012 ................ C12P 7/04

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AoA0K2A0L0. Nov. 11, 2015 (Year: 2015).*
Thomson et al. PLoS One. Feb. 23, 2011;6(2):e17184 (Year: 2011).*
Long et al. African Journal of Microbiology Research vol. 6(18) pp. 4041-4047, May 16, 2012 (Year: 2012).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Andersen, S.J., et al., "Electrolytic extraction drives volatile fatty acid chain elongation through lactic acid and replaces chemical pH control in thin stillage fermentation", Biotechnol Biofuels (2015), pp. 1-14, 8:221.
Gao, C., et al., "Biotechnological routes based on lactic acid production from biomass", Biotechnology Advance (2011), Received Jan. 24, 2011, Received in revised form Jul. 25, 2011, Accepted Jul. 26, 2011, Available online Aug. 6, 2011, pp. 930-939, 29.
Jamshidian, M., et al., "Poly-Lactic Acid: Production, Applications, Nanocomposites, and Release Studies", Comprehensive Reviews in Food Science and Food Safety, 2010, Submitted Mar. 29, 2010, Accepted Jun. 10, 2010, pp. 552-571, vol. 9.
Jeon, B.S., et al., "Production of medium-chain carboxylic acids by Megasphaera sp. MH with supplemental electron acceptors", Biotechnology for Biofuels (2016), pp. 1-9, 9:129.
Juturu, V., et al., "Microbial production of lactic acid: the latest development", Crit Rev Biotechnol, 2016, Received Sep. 1, 2014, Revised May 26, 2015, Accepted May 28, 2015, Published online Aug. 11, 2015, pp. 967-977, 36(6).
Zhu, X., et al., "Production of high-concentration n-caproic acid from lactate through fermentation using a newly solated Ruminococcaceae bacterium CPB6", Biotechnol Biofuels (2017), pp. 1-12, 10:102.

* cited by examiner

*Primary Examiner* — Christian L Fronda
(74) *Attorney, Agent, or Firm* — Scully, Scott, Murphy & Presser, P.C.

(57) ABSTRACT

This disclosure provides a genetically-modified bacterium from the genus *Megasphaera* that comprises an exogenous nucleic acid encoding a bifunctional aldehyde/alcohol dehydrogenase that produces butanol as the final product. The disclosure further provides methods for producing butanol using such genetically-modified bacterium.

9 Claims, 4 Drawing Sheets

Specification includes a Sequence Listing.

SEQUENCE LISTING

```
<160> NUMBER OF SEQ ID NOS: 4

<210> SEQ ID NO 1
<211> LENGTH: 858
<212> TYPE: PRT
<213> ORGANISM: Clostridium acetobutylicum

<400> SEQUENCE: 1

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
```

```
                65                  70                  75                  80
Lys Asn Glu Lys Thr Cys Gly Ile Ile Asp His Asp Ser Leu Gly
                    85                  90                  95

Ile Thr Lys Val Ala Glu Pro Ile Gly Ile Ala Ala Ile Val Pro
                100                 105                 110

Thr Thr Asn Pro Thr Ser Thr Ala Ile Phe Lys Ser Leu Ile Ser Leu
                115                 120                 125

Lys Thr Arg Asn Ala Ile Phe Phe Ser Pro His Pro Arg Ala Lys Lys
    130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                    165                 170                 175

Leu Ser Gln Asp Leu Met Ser Glu Ala Asp Ile Ile Leu Ala Thr Gly
                180                 185                 190

Gly Pro Ser Met Val Lys Ala Ala Tyr Ser Ser Gly Lys Pro Ala Ile
                195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                    245                 250                 255

Tyr Glu Lys Val Lys Glu Glu Phe Val Lys Arg Gly Ser Tyr Ile Leu
                260                 265                 270

Asn Gln Asn Glu Ile Ala Lys Ile Lys Glu Thr Met Phe Lys Asn Gly
                275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                    325                 330                 335

Pro Val Leu Ala Met Tyr Lys Val Lys Asp Phe Asp Glu Ala Leu Lys
                340                 345                 350

Lys Ala Gln Arg Leu Ile Glu Leu Gly Gly Ser Gly His Thr Ser Ser
                355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                    405                 410                 415

Leu Gly Cys Gly Thr Trp Gly Gly Asn Ser Val Ser Gln Asn Val Glu
                420                 425                 430

Pro Lys His Leu Leu Asn Ile Lys Ser Val Ala Glu Arg Arg Glu Asn
                435                 440                 445

Met Leu Trp Phe Lys Val Pro Gln Lys Ile Tyr Phe Lys Tyr Gly Cys
    450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                    485                 490                 495
```

-continued

Ile Thr Lys Val Leu Asp Glu Ile Asp Ile Lys Tyr Ser Ile Phe Thr
            500                 505                 510

Asp Ile Lys Ser Asp Pro Thr Ile Asp Ser Val Lys Lys Gly Ala Lys
        515                 520                 525

Glu Met Leu Asn Phe Glu Pro Asp Thr Ile Ile Ser Ile Gly Gly Gly
530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
    610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
    690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
    770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
    850                 855

<210> SEQ ID NO 2
<211> LENGTH: 12
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature

```
<222> LOCATION: (4)..(9)
<223> OTHER INFORMATION: n stands for any nucleotide

<400> SEQUENCE: 2
gagnnnnnng at                                                        12

<210> SEQ ID NO 3
<211> LENGTH: 14
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (4)..(10)
<223> OTHER INFORMATION: n stands for any nucleotide
<220> FEATURE:
<221> NAME/KEY: misc_feature
<222> LOCATION: (12)..(12)
<223> OTHER INFORMATION: r statnds for "A or G"

<400> SEQUENCE: 3
cagnnnnnnn trtc                                                      14

<210> SEQ ID NO 4
<211> LENGTH: 14
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (4)..(11)
<223> OTHER INFORMATION: n stands for any nucleotide
<220> FEATURE:
<221> NAME/KEY: misc_feature
<222> LOCATION: (13)..(13)
<223> OTHER INFORMATION: r stands for "A or G"

<400> SEQUENCE: 4
cgannnnnnn ntrt                                                      14
```

GENETICALLY-MODIFIED BACTERIA FOR CONVERSION OF ORGANIC COMPOUNDS TO BUTANOL AND METHODS OF USE

CROSS REFERENCE TO RELATED APPLICATION

This application claims the benefit of priority from U.S. Provisional Application No. 62/876,886, filed Jul. 22, 2019, the contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-000R22725 awarded by the U.S. Department of Energy. The government has certain rights in this invention.

INCORPORATION BY REFERENCE OF SEQUENCE LISTING

The Sequence Listing in the ASCII text file, named as 38427_4426.1_Seqlist_ST25.txt of 9 KB, created on Jul. 20, 2020, and submitted to the United States Patent and Trademark Office via EFS-Web, is incorporated herein by reference.

BACKGROUND

The world's energy demand is continually increasing, and the demand is primarily met with fossil fuels, such as petroleum and coal. Due to the increasing energy need, the negative environmental impacts of fossil fuels, and the depletion of the finite fossil fuel sources, renewable energy alternatives need to be used. Many different forms of renewable energy are currently in use, including solar and wind power to replace natural gas and coal with clean electricity, but the production of renewable biofuels is necessary to overcome our oil dependence.

Currently most industrial biofuel production plants use model organisms, like *Saccharomyces cerevisiae* to produce ethanol. Ethanol as a petroleum replacement falls short, though, in comparison to higher chain alcohols, like n-butanol and hexanol. As the carbon chain is extended on the alcohol, the energy density and hydrophobicity increase to become more comparable to gasoline, which makes them a more attractive fuel source. However, unlike ethanol, higher chain alcohols are not produced efficiently and at high yields in nature. Efforts to engineer butanol and hexanol production into model organisms thus far have enabled low levels of production, suggesting that extending the chain elongation pathway beyond a single cycle remains a significant challenge for these engineered pathways in model organisms.

Non-model bacteria have many complex phenotypes of interest which range from tolerance to bioproces sing conditions, like growth at low pH, to the ability to grow on non-traditional substrates. Significant research has gone into a wide variety of feedstocks, from model feedstocks such as glucose to real world substrates such as lignocellulosic biomass and syngas. One feedstock, lactate, holds potential but is currently underutilized. Lactate is routinely produced by lactic acid bacteria at high concentrations and yields and it is able to be produced from a wide variety of feedstocks, including those that do not compete with food sources, such as lignocellulosic hydrolysates. Currently, a major end use of lactate is in the food industry, pharmaceuticals and the production of biodegradable polymer polylactic-acid (PLA). Lactate can be biologically upgraded though by microorganisms and turned into useful products such as medium chain length carboxy-acids. Carboxy-acids act as a platform for the synthesis of a wide variety of commercially important chemicals. While carboxy-acids are produced by many species of bacteria as fermentation end products, only a few biocatalysts have been demonstrated to produce medium chain carboxy-acids from lactate, including mixed culture reactor systems, Ruminococcaceae bacterium CPB6, and *Megasphaera elsdenii*. None of these biocatalysts have been genetically modified which is an important step to developing a platform organism.

*M. elsdenii* belongs to a group of ruminal and intestinal lactate- and glucose-fermenting bacteria called the Negativicutes. *M. elsdenii* produces carboxy acids (C2-C8) as fermentation products when growing on lactate and glucose, including formation of propionic, butyric, hexanoic, and in some cases octanoic acids as major fermentation products.

SUMMARY OF THE DISCLOSURE

In one aspect, the disclosure provides a genetically-modified bacterium from the genus *Megasphaera*, comprising an exogenous nucleic acid encoding a bifunctional aldehyde/alcohol dehydrogenase wherein the bifunctional aldehyde/alcohol dehydrogenase produces butanol as a final product.

In some embodiments, the bifunctional aldehyde/alcohol dehydrogenase is an enzyme from a bacterial species that belongs to the genus *Clostridium*. In some embodiments, the bifunctional aldehyde/alcohol dehydrogenase comprises an amino acid sequence with at least 90% identity to SEQ ID NO: 1. In some embodiments, the exogenous nucleic acid sequence is codon optimized for the species of the genus *Megasphaera* to which the genetically modified bacterium belongs.

In some embodiments, the genetically-modified bacterium is from a *Megasphaera* species selected from the group consisting of *M. hominis*, *M. cerevisiae*, *M. elsdenii*, *M. micronuciformis*, *M. paucivorans*, and *M. sueciensis*. In some embodiments, the genetically-modified bacterium is from the species *M. elsdeni*. In some embodiments, the genetically-modified bacterium is an *M. elsdenii* strain designated as ATCC 25940.

Another aspect of the disclosure is directed to a method for converting an organic compound to butanol, the method comprising inoculating a medium comprising said organic compound with a genetically-modified bacterium from the genus *Megasphaera*, wherein the bacterium comprises an exogenous nucleic acid encoding a bifunctional aldehyde/alcohol dehydrogenase, thereby converting said organic compound to butanol.

In some embodiments, the bifunctional aldehyde/alcohol dehydrogenase is an enzyme from a bacterial species from the genus *Clostridium*.

In some embodiments, the bifunctional aldehyde/alcohol dehydrogenase comprises an amino acid sequence with at least 90% identity to SEQ ID NO: 1.

In some embodiments, the exogenous nucleic acid sequence is codon optimized for the species of the genus *Megasphaera* to which the genetically modified bacterium belongs.

In some embodiments, the organic compound is a carbon source. In some embodiments, the carbon source is a lactate source. In some embodiments, the lactate source is selected from a product of bacterial fermentation, a product of fungal fermentation, a product of chemical synthesis from acetaldehyde and a composition comprising purified lactate.

In some embodiments, the genetically-modified bacterium is from a *Megasphaera* species selected from the group consisting of *M. hominis, M. cerevisiae, M. elsdenii, M. micronuciformis, M. paucivorans*, and *M. sueciensis*

In some embodiments, the genetically-modified bacterium is from the species *M. elsdeni*.

In some embodiments, the genetically-modified bacterium is an *M. elsdenii* strain designated as ATCC 25940.

DETAILED DESCRIPTION OF THE DISCLOSURE

Definitions

Figure 1:
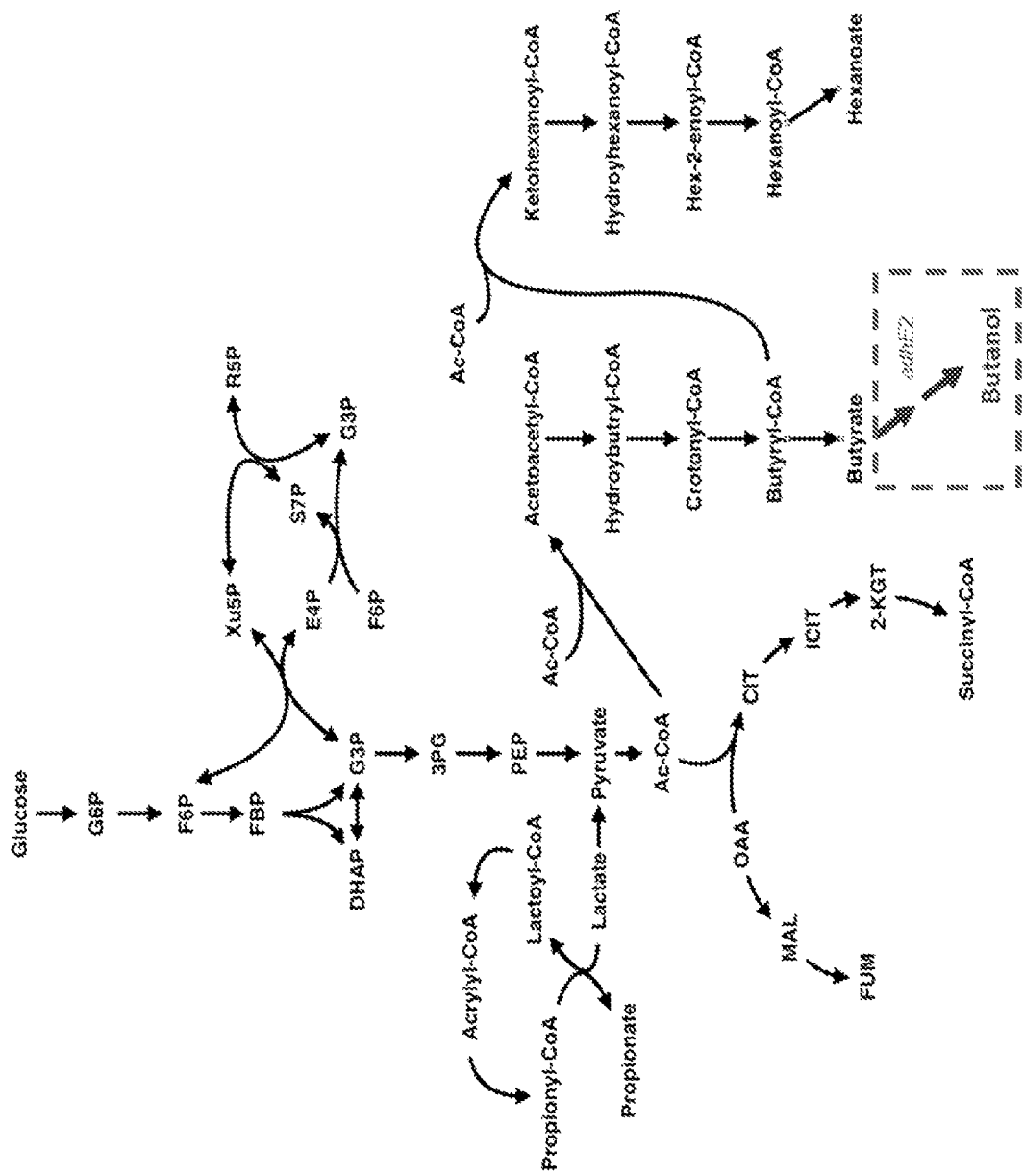
FIG. 1. The biochemical pathways in genus *Megasphaera*. The engineered part of the pathway is shown in a dashed rectangle.

As used herein, the term "about" refers to an approximately ±10% variation from a given value.

The term "cellulose" (also "lignocellulose" or "cellulosic substrate") refers to a structural material that comprises much of the mass of plants. Lignocellulose is composed mainly of carbohydrate polymers (cellulose, hemicelluloses) and an aromatic polymer (lignin).

The term "codon-optimized" refers to nucleic acid molecules that are modified based on the codon usage of the host species (e.g., a specific *Megasphaera* species used), but without altering the polypeptide sequence encoded by the nucleic acid.

As used herein, the term "fermentation" refers to the enzymatic and/or anaerobic breakdown of organic substances by microorganisms (e.g., bacteria and fungi) to produce simpler organic compounds such as alcohols. While fermentation may occur under anaerobic conditions, it is not intended that the term be solely limited to strict anaerobic conditions, as fermentation may also occur under aerobic (e.g., in the presence of oxygen) or microaerobic conditions.

The term "genetically engineered" or "genetically modified" used in connection with a microorganism means that the microorganism comprises a genome that has been modified (relative to the original or natural-occurring genome of the microorganism), or comprises an exogenous introduced nucleic acid.

Disclosed herein are a genetically-modified bacterium from the genus *Megasphaera* that comprises an exogenous nucleic acid encoding a bifunctional aldehyde/alcohol dehydrogenase and methods of producing butanol using the disclosed genetically-modified bacterium.

Genetically-Modified Bacterium

In some embodiments, the present disclosure is directed to a genetically-modified bacterium from the genus *Megasphaera* comprising an exogenous nucleic acid encoding a bifunctional aldehyde/alcohol dehydrogenase that produces butanol as the final product.

In some embodiments, the genetically-modified bacterium is from a *Megasphaera* species selected from the group consisting of *M. hominis, M. cerevisiae, M. elsdenii, M. micronuciformis, M. paucivorans*, and *M. sueciensis*. In a specific embodiment, the genetically-modified bacterium is from the species *M. elsdenii*. In a specific embodiment, the genetically-modified bacterium is an *M. elsdenii* strain designated as ATCC 25940.

In some embodiments, the exogenous nucleic acid sequence is codon optimized for the species of the genus *Megasphaera* to which the genetically modified bacterium belongs.

As used herein, a bifunctional aldehyde/alcohol dehydrogenase refers to an enzyme that can remove hydrogen groups from both an aldehyde and an alcohol. The bifunctional aldehyde/alcohol enzymes of some bacterial strains produce ethanol as the final product. The bifunctional aldehyde/alcohol enzymes of some bacterial strains produce butanol as the final product.

In some embodiments, the bifunctional aldehyde/alcohol dehydrogenase utilized in the instant disclosure comprises the enzymatic activities of both butyryl-CoA dehydrogenase (conversion of butyryl-CoA into butyraldehyde) and butyraldehyde dehydrogenase (conversion of butyraldehyde into butanol) enzymes, i.e., the bifunctional aldehyde/alcohol dehydrogenase utilized in the present disclosure catalyzes the conversion of butyryl-CoA into butyraldehyde, and then the conversion of butyraldehyde into the final product butanol.

In some embodiments, the bifunctional aldehyde/alcohol dehydrogenase gene is from a bacterial species that belongs to the genus *Clostridium*. In some embodiments, the bifunctional aldehyde/alcohol dehydrogenase gene is from the species *Clostridium acetobutylicum*. In a specific embodiment, the bifunctional aldehyde/alcohol dehydrogenase gene encodes a protein which comprises a sequence with at least 90% identity, at least 95% identity, at least 98% identity, at least 99% or greater identity to SEQ ID NO: 1. In some embodiments, the bifunctional aldehyde/alcohol dehydrogenase gene encodes an enzyme with substantially the same level of enzymatic activity as the enzyme having the sequence of SEQ ID NO: 1. In some embodiments, the phrase "substantially the same level of enzymatic activity" when comparing to the enzymatic activity of the enzyme having the sequence of SEQ ID NO: 1, refers to an enzymatic activity that is at least 85%, at least 90%, at least 95%, at least 99% or more of the enzymatic activity of the enzyme having the sequence of SEQ ID NO: 1.

In some embodiments, the exogenous nucleic acid encoding a bifunctional aldehyde/alcohol dehydrogenase that produces butanol as the final product is integrated into the genome of the bacterium. In some embodiments, the exogenous nucleic acid encoding a bifunctional aldehyde/alcohol dehydrogenase that produces butanol as the final product is not integrated into the genome of the bacterium, e.g., remain on a vector such as a plasmid.

Methods for Converting an Organic Compound to Butanol

Another aspect of the disclosure is directed to a method for converting an organic compound to butanol, the method comprising inoculating a medium comprising the organic compound with a genetically-modified bacterium disclosed herein above, i.e., a genetically-modified bacterium from the genus *Megasphaera*, wherein the bacterium comprises an exogenous nucleic acid encoding a bifunctional aldehyde/alcohol dehydrogenase that produces butanol as the final product.

In some embodiments, the genetically-modified bacterium of the claimed method is grown in, or inoculated into, a medium comprising an organic compound. In some embodiments, the medium is a liquid medium, such as a suspension culture medium, or a fermentation broth.

In some embodiments, the organic compound serves, provides or produces a compound that is a carbon source utilized in the butanol production pathway as depicted in FIG. 1. In some embodiments, the organic compound serves, provides or produces a compound that is a carbon source that can break down into the compounds which are utilized in the butanol production pathway. In some embodiments, the organic compound comprises one or more of pyruvate, acetyl-CoA, acetoacetyl-CoA, hydroxybutryl-CoA, crotonyl-CoA, butyryl-CoA and butyrate.

In some embodiments, the organic compound is a lactate source. In some embodiments, the lactate source comprises a product of bacterial or fungal fermentation (e.g., a fermentation broth). In some embodiments, the lactate source comprises a product of chemical synthesis from acetaldehyde. In some embodiments, the lactate source comprises a lignocellulosic biomass. In some embodiments, the lactate source comprises a sugar feedstock. In a specific embodiment, the lactate source comprises lactate, e.g., purified lactate.

In some embodiments, the method comprises inoculating a medium comprising an organic compound with a genetically-modified bacterium from a *Megasphaera* species at an initial concentration of at least $10^3$ cfu/ml, at least $10^4$ cfu/ml, at least $10^5$ cfu/ml, at least $10^6$ cfu/ml, at least $10^7$ cfu/ml, at least $10^8$ cfu/ml, at least $10^9$ cfu/ml, or at least $10^{10}$ cfu/ml.

In some embodiments, the butanol production is achieved when the genetically-modified bacterium is in a log phase of growth, and thus the genetically modified bacterium can be cultured until at least after the bacterium has entered into a log phase of growth. In some embodiments, butanol production is achieved when the genetically-modified bacterium is in a stationary phase of growth, and thus the genetically modified bacterium can be cultured until at least after the bacterium has entered a stationary phase of growth.

In some embodiments, the method comprises growing the bacterium under anaerobic conditions during butanol production. In some embodiments, the anaerobic condition comprises less than 20% oxygen, less than 15% oxygen, less than 10% oxygen, less than 5% oxygen, less than 1% oxygen, or less. In some embodiments, the oxygen is replaced by other gases to provide an anaerobic environment. In some embodiments, the oxygen is replaced by nitrogen, hydrogen, $CO_2$, or a combination thereof. In a specific embodiment, the anaerobic condition comprises about 85% $N_2$, about 10% $CO_2$, and about 5% $H_2$ mixed gas atmosphere.

In some embodiments, the method comprises growing the genetically modified bacterium at about 28° C., about 30° C., about 32° C., about 34° C., about 36° C., about 37° C., about 38° C., or about 40° C. In a specific embodiment, the method comprises growing the genetically modified bacterium at about 37° C.

In some embodiments, the methods of the disclosure result in butanol titers of at least at least 50 mg/L, at least 75 mg/L, at least 100 mg/L, at least 125 mg/L, at least 150 mg/L, at least 175 mg/L, at least 200 mg/L, at least 250 mg/L or higher. In a specific embodiment, the methods result in butanol titer of at least 170 mg/L.

In some embodiments of the present method, the genetically-modified bacterium used is from a *Megasphaera* species selected from the group consisting of *M. hominis, M. cerevisiae, M. elsdenii, M. micronuciformis, M. paucivorans,* and *M. sueciensis*. In a specific embodiment, the genetically-modified bacterium is from the species *M. elsdenii*. In a specific embodiment, the genetically-modified bacterium is an *M. elsdenii* strain designated as ATCC 25940.

In some embodiments of the method, the exogenous nucleic acid sequence is codon optimized for the species of the genus *Megasphaera* to which the genetically modified bacterium belongs.

In some embodiments, the genetically-modified bacterium comprises an exogenous nucleic acid encoding a bifunctional aldehyde/alcohol dehydrogenase that produces butanol as the final product. In some embodiments, the bifunctional aldehyde/alcohol dehydrogenase of the instant disclosure comprises the enzymatic activities of both butyraldehyde dehydrogenase (also called butyryl-CoA reductase, for conversion of butyryl-CoA into butyraldehyde) and butanol dehydrogenase (also called butyraldehyde reductase, for conversion of butyraldehyde into butanol) enzymes, i.e., the bifunctional aldehyde/alcohol dehydrogenase catalyzes the conversion of butyryl-CoA into butyraldehyde, and the conversion of butyraldehyde into the final product butanol.

In some embodiments, the bifunctional aldehyde/alcohol dehydrogenase gene is from a bacterial species that belongs to the genus *Clostridium*. In some embodiments, the bifunctional aldehyde/alcohol dehydrogenase gene is from the species *Clostridium acetobutylicum*. In a specific embodiment, the bifunctional aldehyde/alcohol dehydrogenase gene encodes a protein sequence with at least 90% identity, at least 95% identity, at least 98% identity, at least 99% or greater identity to SEQ ID NO: 1. In some embodiments, the bifunctional aldehyde/alcohol dehydrogenase gene of the instant disclosure encodes an enzyme with substantially the same level of enzymatic activity as the enzyme having the sequence of SEQ ID NO: 1. In some embodiments, the phrase "substantially the same level of enzymatic activity" when comparing to the enzymatic activity of the enzyme having the sequence of SEQ ID NO: 1, refers to an enzymatic activity that is at least 85%, at least 90%, at least 95%, at least 99% or more of the enzymatic activity of the enzyme having the sequence of SEQ ID NO: 1.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1

*M. elsdenii* ATCC 25940 allows for efficient carbon chain elongation that results in longer carbon chain molecules such as butyric acid and hexanoic acid, but it lacks a defined pathway to alcohols. When *M. elsdenii* is grown with lactate as the carbon and energy source, the inventors found that it produces a base level of about 0.4 mM butanol. To engineer *M. elsdenii* for the increased production of alcohols, the bifunctional aldehyde/alcohol dehydrogenase (adhE2) from *Clostridium acetobutylicum* was expressed. This adhE2 preferentially produces butanol from butyryl-CoA (FIG. 1).

Figure 2:
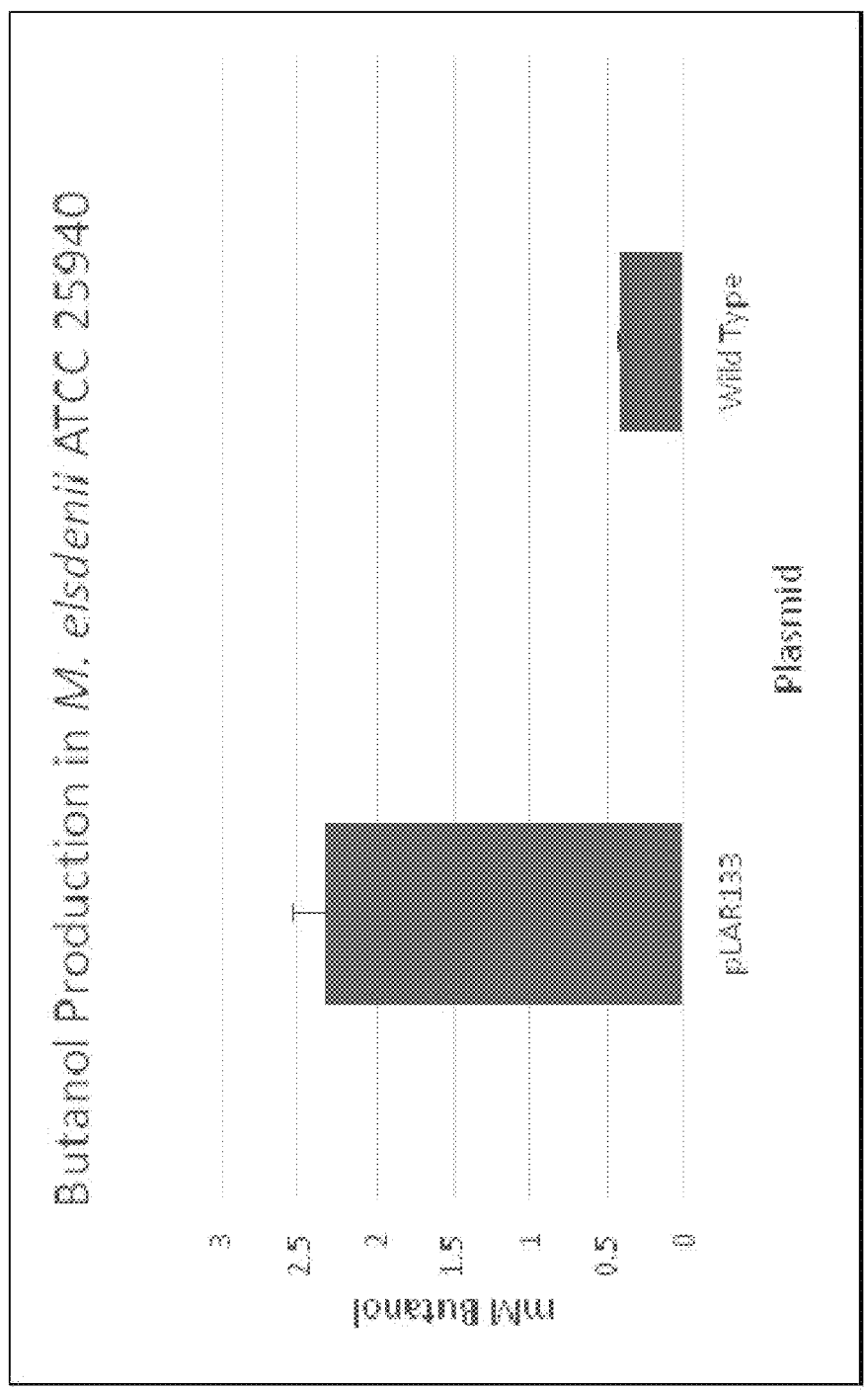
FIG. 2. Production of butanol by *M. elsdenii* (ATCC 25940) expressing an empty plasmid (Wild Type) or a plasmid encoding a bifunctional aldehyde/alcohol dehydrogenase (pLAR133). Values represent the average of three replicates, with error bars indicated the standard deviation in among the three samples.

Initially, adhE2 was expressed in *M. elsdenii* ATCC 25940 on a plasmid under control of the T5lac promoter. No alcohol production was detected in the strain. Therefore, a proteomics experiment was performed to determine if there was sufficient expression of adhE2 using the T5lac promoter. Proteomics revealed Adhe2 was in the top 20% of proteins, but in other alcohol producing organisms the AdhEs are often in the top 1% of expressed proteins. This suggests that there isn't high enough expression of adhE2 in the current conditions. Therefore, to increase adhE2 expression, the promoter driving highly expressed ribosomal S4 protein was identified using the proteomics data set. The adhE2 gene was cloned under the control of this native *M. elsdenii* promoter, and strains containing this construct (pLAR133) produced 2.3 mM butanol from lactic acid as a growth substrate (FIG. 2), or 11% of the maximum theoretical yield.

This engineered *M. elsdenii* strain is superior to existing technology because this organism has high flux through the carbon chain elongation pathway and the flux is superior to other organisms that have been engineered before. This gives it the potential to have a higher butanol yield than other model organisms. Currently other organisms have a greater yield of butanol from glucose, but this is the first-time butanol production has been demonstrated in microorganisms using lactate as the carbon source.

Example 2: Methylome Analysis of *M. elsdenii* ATCC 25940 and NCIMB 702410

To enable transformation and overcome the native RM systems in both strains of *M. elsdenii* the RM systems were identified and tested for functionality. *M. elsdenii* ATCC 25940 encodes two type I systems (Mels_0050-0052, Mels_1615-1617), two type II (Mels_0974-0976, Mels_1947), and two type IV systems (mels_1373, mels_2001-2002). *M. elsdenii* NCIMB 702410 encodes one type I system (C6Y28_02465-02475), two type II systems (C6Y28_01935-01940, C6Y28_04345), and two type IV systems (C6Y28_00750, C6Y28_09510-09515). Methylome analysis was performed to determine which of the methylation subunits are active in both strains. Methylated motifs were determined using Single Molecule Real-Time sequencing (SMRT) on the PacBio platform and Whole genome bisulfite sequencing (WGBS) using Illumina. SMRT analysis revealed two type I motifs and gAtc in *M. elsdenii* ATCC 25940 and one type I motif in NCIMB 702410 while WGBS did not reveal any $m^5C$ motifs in either strain (Table 1). Methylome data reveals the type I methyltransferases in both strains are active. According to the NEB Restriction Enzyme Database (REBASE)(Roberts R J. et al., *Nucleic Acids Research*. 2015; 43(D1):D298-D9) the type II, Mels_0974-0976, is predicted to act on gAtc which indicates it is the active methyltransferase while the other type II systems are not active.

TABLE 1

Methylome analysis and transformation efficiencies of *M. elsdenii* ATCC 25940 and NCIMB 70241. The methylated base is capitalized in each motif. Transformation efficiencies are reported in colony forming units per microgram of DNA (CFU/µg) for each plasmid successfully transformed. Plasmids were isolated out of the best methylation strain, no colonies formed using wild type *E. coli*

| Strain | Methylome | Transformation Efficiency | | |
|---|---|---|---|---|
| | | pMTL85141 | pBC1-CAT | pVJL1-cat |
| ATCC 25940 | gAtc<br>gAgnnnnnngat (SEQ ID NO: 2)<br>cAgnnnnnnnTrtc (SEQ ID NO: 3)) | 10000 | 4500 | 2000 |
| NCIMB 702410 | cgAnnnnnnnnTrtc (SEQ ID NO: 4) | 2020 | X | X |

Example 3: Expression of Methyltransferases in *E. coli*

To mimic the *M. elsdenii* methylome the corresponding methyltransferases to were expressed from the *E. coli* chromosome. Expression of methyltransferases in *E. coli* enables proper methylation of plasmids prior to transformation in *M. elsdenii*. For ATCC 25940 both type I methyltransferases and DNA specificity subunits were integrated into the *E. coli* chromosome. An *E. coli* dam+dcm- strain was utilized so that Dam will methylate gAtc and Dcm methylation won't interfere with the type IV restriction enzymes in the strain. For NCIMB 702410 the type I methyltransferase and DNA specificity subunits were integrated into an *E. coli* dam-dcm- strain. Neither of the *E. coli* motifs were seen in the methylome data therefore the NCIMB 702410 type I motif was integrated into an *E. coli* strain lacking Dam and Dcm methylation. Each of the *E. coli* methylation strains were sent for methylome analysis, via SMRT sequencing, to determine if the methyltransferases are functional. Analysis determined both strains mimic their corresponding *M. elsdenii* strain.

Example 4: Successful Transformation of *M. elsdenii* ATCC 25940 and NCIMB 702410

To enable transformation for the first time in this species, multiple plasmids with different origins of replication were tested. The origins of replication tested include, pBP1, pCB102, pCD6, and pIM13 from the pMTL8000 series (Heap J. T. et al., *Journal of microbiological methods*. 2009; 78(1):79-85) and others, pNW33N (Riley L. A. et al., *J Ind Microbiol Biotechnol*. 2019), pBC1, and pVJL1. The pMTL8000 series, pNW33N, and pBC1 are known Clostridia and *Bacillus* spp. origins of replication while pVJL1 comes from *Veillonella* spp. which is the closest genetically tractable organism phylogenetically to *Megasphaera*. Each of these plasmids were isolated out of wild type *E. coli* (dam+dcm−) and the best methylation strain for each strain of *M. elsdenii*. Transformation was performed using electroporation. No transformation was demonstrated with any plasmid isolated out of wild type *E. coli*. The pMTL85141 (pIM13), pVJL1-cat, and pBC1-cat plasmids were successfully transformed into both strains of *M. elsdenii* when properly methylated to mimic the methylome. Each plasmid had similar transformation efficiencies with the best being 10000 colony forming units per microgram of DNA (CFU/µg) for ATCC 25940 and 2020 CFU/µg for NCIMB 702410 (Table 1).

Example 5: Butanol Production in *M. elsdenii* ATCC 25940

Butanol production was enabled in *M. elsdenii* to demonstrate metabolic engineering of this species. To enable butanol production, four plasmids were constructed with adhE2 from *Clostridium acetobutylicum*. The bifunctional aldehyde/alcohol dehydrogenase, adhE2, has been demonstrated to have a high affinity for converting butyryl-CoA to butyrylaldehyde to butanol while other characterized adhE preferentially convert acetyl-CoA to ethanol (Atsumi S. et al., *Metabolic engineering*. 2008; 10(6):305-11; Fontaine L. et al., *Journal of bacteriology*. 2002; 184(3):821-30). There are no characterized promoters in *M. elsdenii*; therefore, to enable high concentrations of AdhE2 four different expression plasmids were tested. The first used pTac to drive expression which is a native *E. coli* promoter that enables high expression. Next, the UP-element in pTac was replaced with the UP-element from *M. elsdenii* ATCC 25940 16S rRNA gene. A native promoter from *M. elsdenii* was then used. Mels_747 encodes a butyryl-coA transferase and is a part of central carbon metabolism. Central metabolism genes are often highly expressed therefore 300 base pairs upstream of the gene were used to drive adhE2. Finally, expression of cat in pMTL85141 is sufficient for thiamphenicol resistance in *M. elsdenii*, so adhE2 was placed downstream of cat to utilize the same promoter.

Figure 3A:
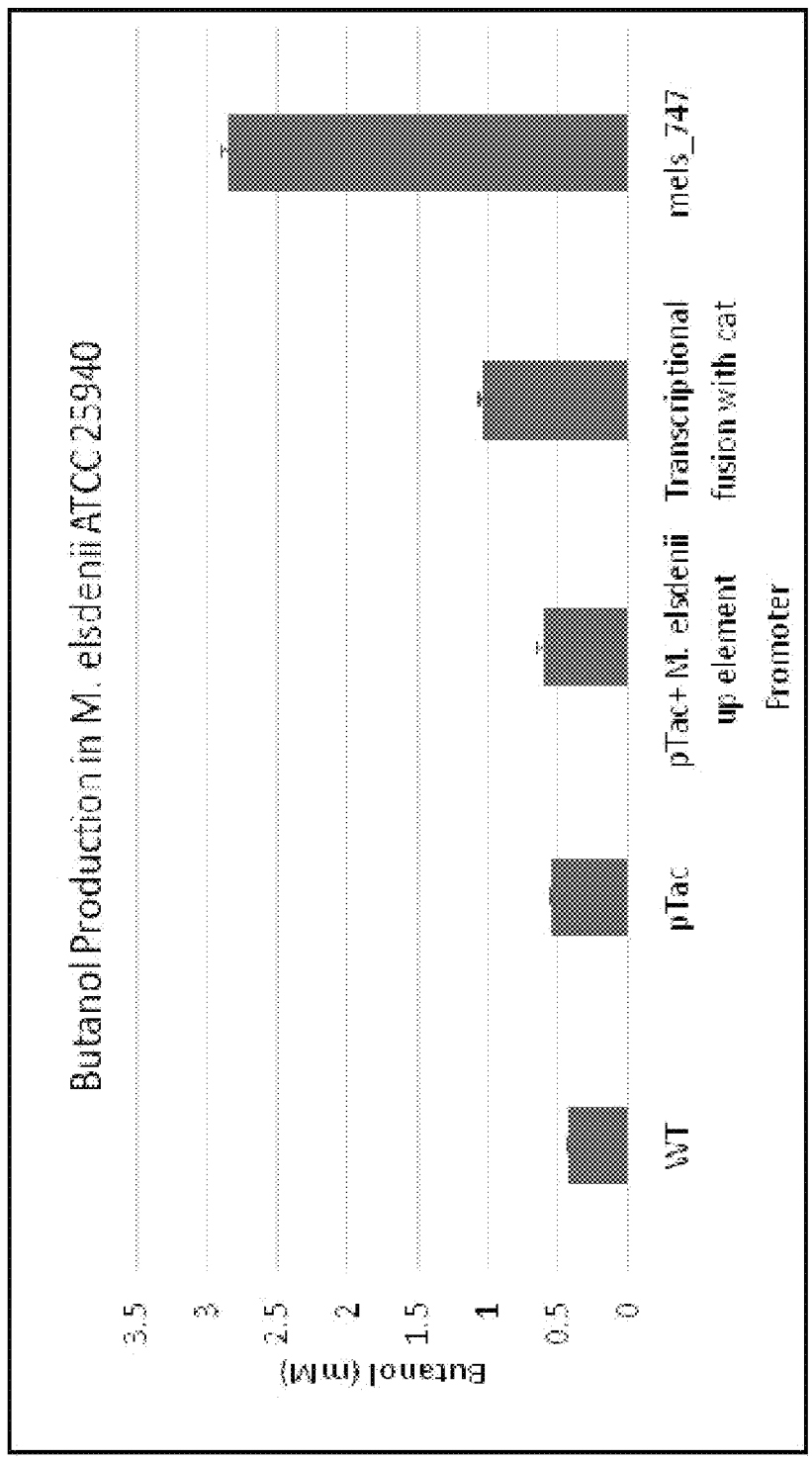
FIGS. 3A-3B. Fermentation products in *M. elsdenii* ATCC 25940 using adhE2 under control of four different promoters. (A) Butanol production (B) Complete fermentation profile of *M. elsdenii* ATCC 25940. In the bar graphs shown in FIG. 3B, production of each fermentation product using the following promoters is shown (from left to right): pTac, pTac+*M. elsdenii* UP element, Mels_747, Transcriptional fusion with cat, and wild type (WT).
Figure 3B:
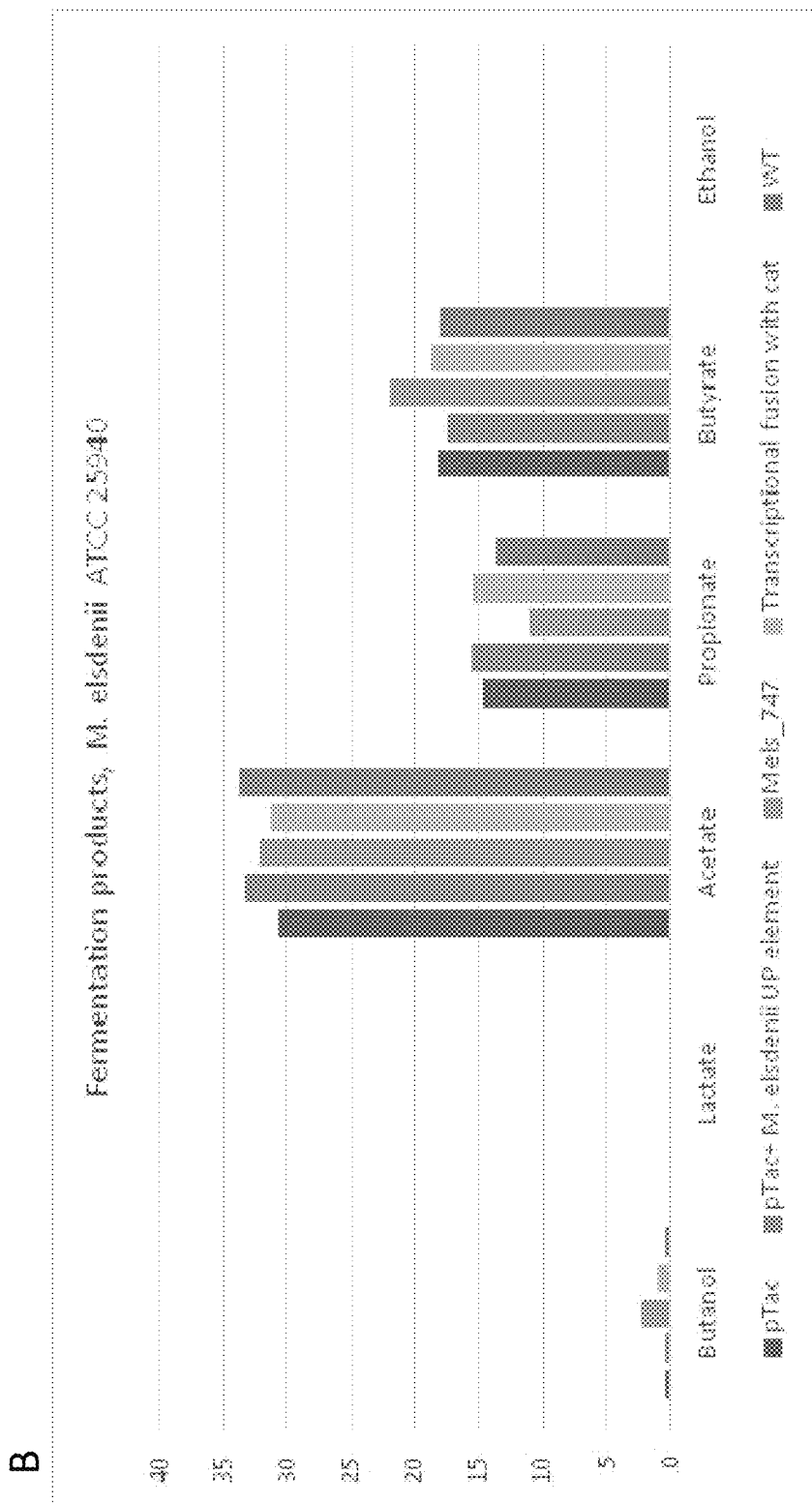

Each of these plasmids were transformed into both strains of *M. elsdenii* and fermentations were performed using two growth conditions, media with 5 g/L glucose and 5 g/L lactate. *M. elsdenii* was grown in each condition for 48 hours and samples were end point samples were taken for quantification of the carbon substrates and fermentation products using HPLC. No butanol was observed in the NCIMB 702410 strain from either carbon substrate and no butanol was observed when ATCC 25940 was grown on glucose. Wild type *M. elsdenii* ATCC 25940 natively demonstrated low levels of butanol production, ~0.5 mM, when grown on lactate with similar levels when adhE2 is expressed with pTac and the modified pTac containing a *Megasphaera* UP-element. Double the butanol was demonstrated using a transcriptional fusion with cat. The highest butanol concentration, 2.5 mM, was demonstrated using the native *M. elsdenii* promoter (FIG. 3A). Butanol production is 10.2% of theoretical from lactate. The other fermentation products, acetate, propionate, and butyrate remained similar in all strains except the native promoter where propionate was decreased by about 5 mM. The media used contains 36 mM sodium acetate so high levels of acetate are indicative of the media composition (FIG. 3B).

Example 6: Integration of adhE2 into the Chromosome of *M. elsdenii* ATCC 25940

To further optimize butanol production in ATCC 25940, the native Mels_747 promoter and adhE2 were integrated into the chromosome. The gene uracil phosphoribosyltransferase (mels_2191), upp, was targeted as the integration site. This gene has been used as a counter selectable marker in a variety of bacteria where 5-fluororuricil is toxic when upp is present (Solem C. et al., *Applied and Environmental Microbiology*. 2008; 74(15):4772, Shi T. et al., *PLoS One*. 2013; 8(11):e81370). Using a homologous recombination approach, an adhE2 insertion vector was constructed with 1 kb homology arms upstream and downstream of upp flanking adhE2, in the multiple cloning site of a replicating vector, pMTL85141. The vector was transformed into *M. elsdenii* ATCC 25940, colonies were picked into media supplemented with thiamphenicol, transferred to media only, and finally plated on 5-fluorouricil to select for colonies where adhE2 was integrated into the chromosome in place of upp. The adhE2 successfully replaced upp using this method and fermentations were performed with this strain to determine butanol concentrations.

Example 7: Materials and Methods

Growth and Media Conditions

*M. elsdenii* ATCC 25940 and NCIMB 702410 (Hatmaker E. A. et al., *Microbiology Resource Announcements*. 2019; 8(3):e01430-18) were grown in Reinforced Clostridial Media (RCM) either with (BD Difco) or without 0.5 g/L agar (HIMEDIA) as indicated. A modified RCM was also used for fermentations containing 5 g/L 60% (w/w) sodium D-lactate in place of glucose. Each type of RCM was supplemented with 0.5 ml/L 0.2% (w/v) resazurin as a redox indicator. Growth occurred at 37° C. in a Coy vinyl anaerobic chamber with 85% $N_2$, 10% $CO_2$, and 5% $H_2$ mixed gas atmosphere. Media was supplemented with 5 µg/mL thiamphenicol for plasmid selection.

Methylome Analysis

*M. elsdenii* genomic DNA was prepped using the Qiagen genomic tip kit according the manufacturer's instructions. Genomic DNA was sent to the Joint Genome Institute (JGI) for sequencing using Single Molecule Real-Time (SMRT) sequencing on the Pacific Biosciences (PacBio) platform (Hatmaker E. A. et al., *Microbiology Resource Announcements*. 2019; 8(3):e01430-18). Methylated motifs were determined using the SMRT Analysis software and Expression Analysis (Flusberg B. A. et al., *Nature methods*. 2010; 7(6):461-5). For whole genome bisulfite sequencing (WGBS), methylC-seq libraries were formed and sequenced via Illumina, methylated motifs were determined as previously described (Riley L. A. et al., J Ind Microbiol Biotechnol. 2019).

Methyltransferase Expression in *E. coli*

Each methyltransferase was cloned into pLAR067, under control of the arabinose-inducible pBad, using Gibson assembly. For *M. elsdenii* ATCC 25940 each of the type I methyltransferases and DNA specificity subunits were codon optimized and synthesized, while the NCIMB 702410 type I system was PCR amplified from the genome. Mels_0050-51 was inserted into pLAR067 with an R4 attP site following it, mels_1615-16 was inserted into pLAR067 without an attP site, and C6Y28_02465-02475 was inserted into pLAR067 with an BxB1 attP site. Mels_1615-1616 was integrated into the E. coli WM3118 Δdcm::frt chromosome using methods previously described and mels_0050-51 was integrated next using the conditional-replication, integration, and modular (CRIM) system (Haldimann A. et al., Journal of Bacteriology. 2001; 183(21):6384-93). C6Y28_02465-02475 was integrated into E. coli BW25113 Δdcm::frt Δdam::frt chromosome using methods previously described.

Plasmids of interest for transformation of M. elsdenii were transformed into each of the E. coli methylation strains and cultures of each plasmid were grown with 1 mM arabinose for methyltransferase expression induction. Each of the plasmids were prepped using ZymoPure II plasmid midiprep kit. The pMTL8000 series were used for transformation of M. elsdenii (Heap J. T. et al., Journal of microbiological methods. 2009; 78(1):79-85). Plasmids containing other origins, pBC1 and pVJL1 (Liu J. et al., Applied and environmental microbiology. 2012; 78(9):3488-91), were also used. To construct these plasmids each origin was synthesized into pNJ022 and the pNW33N origin was replaced with cat using Gibson assembly.

Transformation of M. elsdenii

Overnight cultures of M. elsdenii were grown in 5 mL RCM with 0.5 g/L agar (Himedia). Next, 50 µL was sub-cultured into 500 mL RCM (BD Difco), in duplicate, and grown overnight to stationary phase. All competent cell preparation was done at room temperature. To make competent cells, cells were spun down at 5,000×g in 500 mL centrifuge bottles for 10 minutes. Supernatant was decanted and cells were washed by resuspending the cell pellet in 250 mL electroporation buffer (250 mM sucrose, 10% glucose). Cells were spun again and washed twice more. After the last wash the electroporation buffer was completely removed, and cells were resuspended in enough electroporation buffer to enable pipetting (~500 uL) and transferred to a microcentrifuge tube. 20 µL of fresh electrocompetent cells were transformed with 1 µg of DNA, in duplicate. A 1 mM cuvette was used and shocked with a square wave at 1200 v and 1.5 ms. After electroporation cells were recovered in 1 mL RCM with 0.5 g/L agar and incubated for 3 hours. Cells were then plated in molten RCM+1.5% agar, and once the agar plates solidified, they were incubated for 2-3 days. Colonies were verified by PCR for the plasmid backbone.

Construction of Butanol Expression Vectors

Butanol expression vectors were constructed using Gibson assembly according to the manufacturer's instructions and each part was PCR amplified. The Clostridium acetobutylicum adhE2 was inserted into the MCS of pMTL85141 under control of three different promoters. The first construct, pLAR131, utilized pTac. The second construct, pLAR132, replaced the up element of pTac with the UP element from the M. elsdenii 16S rRNA gene. The third construct, pLAR133, a native M. elsdenii promoter was used by amplifying 300 bp upstream of mels_747. Finally, for pLAR135 the adhE2 was inserted with a Ribosomal binding site (RBS) plus 7 bases following cat in pMTL85141.

Fermentation and Product Quantification

M. elsdenii ATCC 25940 and NCIMB 702410 wild type and each strain containing the butanol expression vectors were grown in 5 mL RCM (himedia)+thiamphenicol overnight. 50 uL of each strain was added to Balch tubes containing 10 mL of RCM (BD Difco) and modified RCM plus lactate. Each strain was grown in triplicate for 48 hours. Samples were taken and fermentation products were quantified using High Performance Liquid Chromatography (HPLC). Lactate, glucose, acetate, butyrate, valerate, and butanol were quantified on Breeze HPLC system with the Aminex-HPX-87H column (Bio-Rad). The mobile phase was 5 mM sulfuric acid.

Integration of adhE2 into the Chromosome

A plasmid to integrate adhE2 under control of the mels_747 promoter into upp was constructed by Gibson assembly. 1 kb homology arms upstream and downstream of upp were cloned flanking adhE2 into the MCS of pMTL85141. All E. coli growth was done at room temperature to enable correct construction of the homology arms. The plasmid was transformed into M. elsdenii ATCC 25940 and colonies were subsequently picked into RCM+5 µg/mL TM. The liquid cultures were passaged into RCM. Next the culture was serial diluted in quad petri plates with RCM+ 1.5% agar+20 µg/mL 5-fluorouricil. The plates were incubated overnight, and colonies were streaked out on RCM plates. Single colonies were picked into RCM (himedia) and PCR screened for insertion into upp. M. elsdenii ATCC 25940 Δupp::adhE2 was tested for butanol production in triplicate in modified RCM plus lactate with the wild type control.

What is claimed is:

1. A genetically-modified bacterium of *Megasphaera elsdenii*, comprising a sole exogenous nucleic acid of a carbon chain elongation pathway encoding a bifunctional aldehyde/alcohol dehydrogenase, wherein the bifunctional aldehyde/alcohol dehydrogenase produces butanol as a final product and comprises an amino acid sequence with at least 90% identity to SEQ ID NO: 1, and wherein the genetically-modified bacterium has increased butanol production using lactate as the carbon source compared to a wild type *Megasphaera* elsdenii.

2. The genetically-modified bacterium of claim 1, wherein the bifunctional aldehyde/alcohol dehydrogenase is an enzyme from a bacterial species that belongs to the genus *Clostridium*.

3. The genetically-modified bacterium of claim 1, wherein the exogenous nucleic acid sequence is codon optimized for *Megasphaera elsdenii*.

4. The genetically-modified bacterium of claim 1, wherein the genetically-modified bacterium is an *M. elsdenii* strain designated as ATCC 25940.

5. A method for converting an organic compound to butanol, the method comprising inoculating a medium comprising said organic compound with the genetically-modified bacterium of claim 1, thereby converting said organic compound to butanol, wherein the organic compound is lactate.

6. The method of claim 5, wherein the bifunctional aldehyde/alcohol dehydrogenase is an enzyme from a bacterial species from the genus *Clostridium*.

7. The method of claim 5, wherein the exogenous nucleic acid sequence is codon optimized for *Megasphaera* elsdenii.

8. The method of claim 3, wherein the lactate is a product of bacterial fermentation, a product of fungal fermentation, a product of chemical synthesis from acetaldehyde, or a composition comprising purified lactate.

9. The method of claim 5, wherein the genetically-modified bacterium is an *M. elsdenii* strain designated as ATCC 25940.

* * * * *